United States Patent [19]

Choi et al.

[11] Patent Number: 6,140,532
[45] Date of Patent: *Oct. 31, 2000

[54] O-CARBAMOYL-PHENYLALANINOL HAVING SUBSTITUENT AT BENZENE RING, ITS PHARMACEUTICALLY USEFUL SALTS AND METHOD FOR PREPARING THE SAME

[75] Inventors: Yong Moon Choi, Towaco, N.J.; Dong Il Han, Yusung-ku, Rep. of Korea; Yong Kil Kim, Yusung-ku, Rep. of Korea; Hun Woo Shin, Yusung-ku, Rep. of Korea

[73] Assignee: SK Corporation, Fairfield, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/629,620

[22] Filed: Apr. 9, 1996

[30] Foreign Application Priority Data

Apr. 10, 1995 [KR] Rep. of Korea .......................... 95-8310

[51] Int. Cl.$^7$ .................................................. C07C 261/00
[52] U.S. Cl. ............................................. 560/164; 560/163
[58] Field of Search ...................................... 560/163, 164

[56] References Cited

U.S. PATENT DOCUMENTS 5,705,640 1/1998 Choi ........................................ 560/163
5,756,817 5/1998 Choi ........................................ 560/163

*Primary Examiner*—Michael L. Shippen
*Attorney, Agent, or Firm*—Gibbons, DelDeo, Dolan, Griffinger & Vecchione

[57] ABSTRACT

O-Carbamoyl-phenylalaninol having substituent at benzene ring, represented by the general formula I, and pharmaceutically useful salts thereof, which are useful for the prophylaxis and treatment of CNS disorder including depression and anxiety, are disclosed:

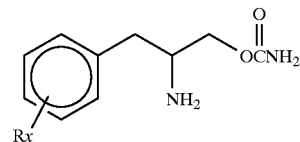

wherein R is lower alkyl containing 1 to 8 carbon atoms, halogen such as F, Cl and I, alkoxy containing 1 to 3 carbon atoms, thioalkoxy containing 1 to 3 carbon atoms, nitro, hydroxy, or trifluorocarbon, and x is an integer of 1 to 3, with a proviso that R is the same or different when x is 2 or 3.

2 Claims, No Drawings

O-CARBAMOYL-PHENYLALANINOL HAVING SUBSTITUENT AT BENZENE RING, ITS PHARMACEUTICALLY USEFUL SALTS AND METHOD FOR PREPARING THE SAME

BACKGROUND OF THE INVENTION

1. Field of the Invention

The present invention relates, in general, to novel phenylalkylamino carbamate compounds and pharmaceutically useful salts thereof. More particularly, the present invention relates to O-carbamoyl-phenylalaninol having substituent at benzene ring and pharmaceutically useful salts thereof, which are useful to treat deseases of the central nervous system such as depression and anxiety. Also the present invention is concerned with methods for preparing the same.

2. Description of the Prior Art

One of important therapeutical medicines useful for controlling central nervous system (hereinafter referred to as "CNS") disorders is phenylethylamine derivatives. These compounds have been used mainly to treat obesity, narcolepsy, minimal brain dysfunction and mild depression.

Carbamates have been effectively used for controlling CNS disorders. For example, 2-methyl-2-propyl-1,3-propanediol dicarbamate was reported in J. Am. Chem. Soc., 73, 5779 (1951) and the pharmaceutical activity thereof was ascertained in J. Pharmacol. Exp. Ther., 104, 229 (1952).

U.S. Pat. No. 2,884,444 discloses 2-phenyl-1,3-propanediol dicarbamate and U.S. Pat. No. 2,937,119 discloses isopropyl meprobamate. These carbamate compounds are found to be very effective therapeutic medicines for treating CNS disorders, especially, as an antiepileptic and a centrally acting muscle relaxant. Research for the development of carbamate therapeutics for CNS diseases has been and continues to be actively advanced.

Recent design of pharmacologically useful compounds has been based on amino acids or the derivatives thereof, which is mainly attributable to the fact at many of the compounds found in biological systems come from amino acids or the derivatives thereof. In addition, in most cases, the function of a pharmaceutically useful compound is effected after it binds to an enzyme or receptor, which may trigger the regulatory mechanisms of the enzyme or receptor.

SUMMARY OF THE INVENTION

Intensive researches repeated by the present inventors aiming to develop therapeutics for CNS disorders have resulted in finding that O-carbamoyl-phenylalaninol having substituent at benzene ring and pharmaceutically useful salts thereof are pharmaceutically useful for prophylaxis or treatment of CNS disorders, such as depression and anxiety.

Accordingly, it is a principal object of the present invention to provide novel O-carbamoyl-phenylalaninol having substituent at benzene ring and pharmaceutically acceptable salts thereof.

It is another object of the present invention to provide a method for preparing O-carbamoyl-phenylalaninol having substituent at benzene ring and pharmaceutically acceptable salts thereof.

DETAILED DESCRIPTION OF THE INVENTION

In accordance with an aspect of the present invention, there are provided novel O-carbamoyl-phenylalaninol having substituent at benzene ring, represented by the following general formula I:

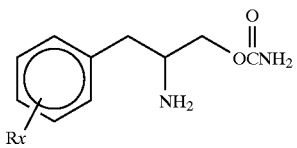

[I]

wherein R is lower alkyl containing 1 to 8 carbon atoms, halogen such ask F, Cl and I, alkoxy containing 1 to 3 carbon atoms, thioalkoxy containing 1 to 3 carbon atoms, nitro, hydroxy, or trifluorocarbon, and x is an integer of 1 to 3, with a proviso that R is the same or different when x is 2 or 3, and pharmaceutically acceptable salts thereof.

In accordance with another aspect of the present invention, novel O-carbamoyl-phenylalaninol having substituent at benzene ring, represented by the general formula I and pharmaceutically useful salts thereof, which are useful for the prophylaxis and treatment of CNS disorders including depression and anxiety, can be prepared by the following steps:

reacting N-t-butyloxycarbonyl phenylalaninol having substituent at benzene ring with 1,1'-carbonyldiimidazole and then with ammonia, without purification in a solution, to synthesize O-carbamoyl-N-t-butyloxycarbonyl phenylalaninol having substituent at benzene ring;

deprotecting the O-carbamoyl-N-t-butyloxycarbonyl phenylalaninol having substituent at benzene ring with aqueous hydrochloric acid solution to give O-carbamoyl-phenylalaninol having substituent at benzene ring, represented by the general formula I; and treating O-carbamoyl-phenylalaninol having substituent at benzene ring with an anhydrous acid in a solution without further purification, to give pharmaceutically acceptable salts thereof.

In accordance with another aspect of the present invention, novel O-carbamoyl-phenylalaninol having substituent at benzene ring, represented by the general formula I and pharmaceutically useful salts thereof, which are useful for the prophylaxis and treatment of CNS disorders including depression and anxiety, can also be prepared by the following steps:

reacting N-benzyloxycarbonyl phenylalaninol having substituent at benzene ring with 1,1'-carbonyldiimidazole and then with ammonia, without purification in a solution, to synthesize O-carbamoyl-N-benzyloxycarbonyl phenylalaninol having substituent at benzene ring;

deprotecting the O-carbamoyl-N-benzyloxycarbonyl phenylalaninol compound by hydrogenation in the presence of a catalyst to give O-carbamoyl-phenylalaninol having substituent at benzene ring, represented by the general formula I; and treating O-carbamoyl-phenylalaninol having substituent at benzene ring with an anhydrous acid in a solution without further purification, to give pharmaceutically acceptable salts thereof.

The first method for preparing the novel compounds of the general formula I will be in detail described below.

N-t-butyloxycarbonyl-phenylalaninol having substituent at benzene ring, represented by the general formula II;

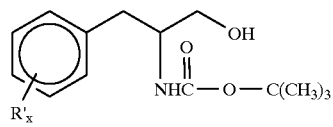

[II]

wherein R' is lower alkyl containing 1 to 8 carbon atoms, halogen such as F, Cl and I, alkoxy containing 1 to 3 carbon atoms, thioalkoxy containing 1 to 3 carbon atoms, nitro, t-butyloxycarbonyloxy, or trifluorocarbon, and x is an integer of 1 to 3, with a proviso that R' is the same or different when x is 2 or 3, is reacted with 1,1'-carbonyldiimidazole in an ethereal solution, a halogenated hydrocarbon solution or the mixtures thereof, followed by the treatment of ammonia gas, to yield O-carbamoyl-N-t-butyloxycarbonyl phenylalaninol having substituent at benzene ring represented by the general formula III:

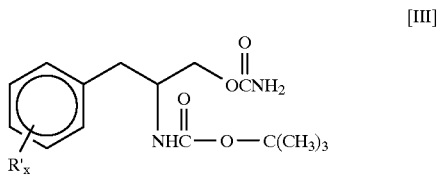

wherein R' and x each are as defined above. Then, this intermediate is deprotected by aqueous hydrochloric acid solution. As a result of the deprotection, there is obtained o-carbamoyl-phenylalaninol having substituent at benzene ring, represented by the general formula I:

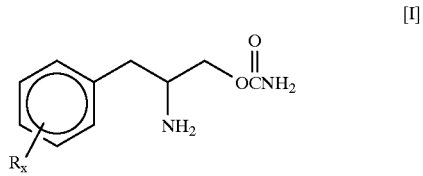

wherein R and x each are as defined above. Without further purification, the compound of formula I may be converted into pharmaceutically acceptable salts through treatment with anhydrous acid in a solution.

This procedure is summarized as set forth in Reaction Scheme I below.

In the reaction scheme I, HX represents an acid capable of forming a pharmacologically useful salt with the basic nitrogen atom.

Details of the reaction conditions described in Reaction Scheme I are as follows. In the first step, the concentration of the starting material (II) is about 0.005 to 3 moles with 1,1'-carbonyldiimidazole ranging from about 1.0 to 2.0 equivalents. This reaction is preferably carried out at a temperature of −10 to 70° C. Without purification, the resulting intermediate is treated with 1 to 1,000 equivalents of ammonia at a temperature of −30 to 30° C., to give the compound of the general formula III. For this carbamoylization, an ethereal solvent such as diethyl ether and tetrahydrofuran, a halogenated hydrocarbon solvent such as dichloromethane and chloroform, or the mixtures thereof may be used.

0.005 to 3 moles of the compound of the general formula III is treated with aqueous 1 to 12N hydrochloric acid at a temperature of −10 to 30° C., followed by neutralization.

The second method for preparing the novel compounds of the general formula I will be in detail described below.

N-benzyloxycarbonyl-phenylalaninol having substituent at benzene ring, represented by structural formula II':

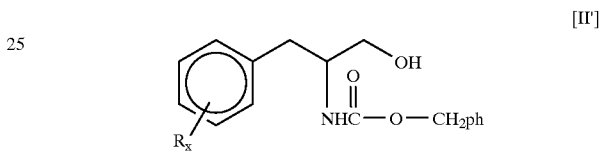

wherein R is lower alkyl containing 1 to 8 carbon atoms, halogen such as F, Cl and I, alkoxy containing 1 to 3 carbon atoms, thioalkoxy containing 1 to 3 carbon atoms, nitro, hydroxy, or trifluorocarbon, and x is an integer of 1 to 3, with a proviso that R is the same or different when x is 2 or 3, is reacted with 1,1'-carbonyldiimidazole in an ethereal solution, a halogenated hydrocarbon solution or the mixtures thereof, followed by the treatment of ammonia gas, to yield O-carbamoyl-N-benzyloxycarbonyl phenylalaninol having substituent at benzene ring, represented by the general formula III':

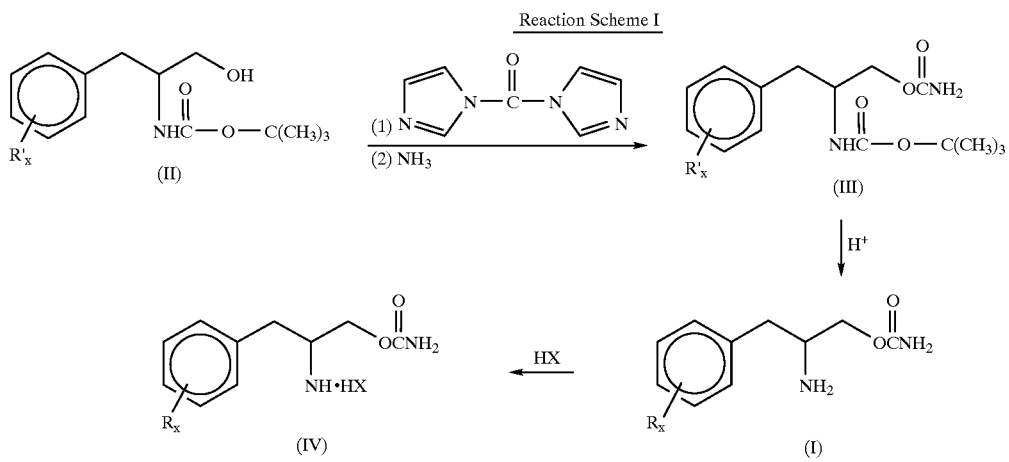

Reaction Scheme I

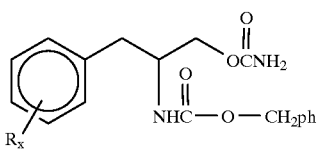

wherein R and x each are as defined above. Then, this intermediate is deprotected by hydrogenation in the presence of a catalyst. As a result of the deprotection, there is obtained O-carbamoyl-phenylalaninol having substituent at benzene ring, represented by the general formula I:

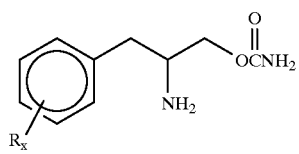

wherein R and x each are as defined above. Without further purification, the compound of formula I may be converted into pharmaceutically acceptable salts through treatment with anhydrous acid in a solution.

This procedure is summarized as set forth in Reaction Scheme II below.

0.005 to 3 mole of the compound of the general formula III' is deprotected by hydrogenation at a temperature of −10 to 150° C. under hydrogen atmosphere of 1 to 100 atm. The hydrogenation from Compound III' to Compound I is carried out in an ethereal solvent such as tetrahydrofuran, an alcoholic solvent such as methanol, water, an aromatic hydrocarbon solvent such as toluene, benzene and xylene, an ester solvent such as ethyl acetate or the mixtures thereof. This reaction is performed in the presence of a catalyst such as palladium, platinum, oxides of platinum, rhodium, or iridium.

Concrete examples of the anhydrous acid used for the preparation of Compound IV from Compound I include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid. Additional acids can be referred to "Pharmaceutical Salts", J. Pharm. Sci., 1977; 66(1): 1–19. This preparation is executed in a reaction media which can be exemplified by an ethereal solvent such as tetrahydrofuran, an alcoholic solvent such as methanol, an ester solvent such as ethyl acetate, a halogenated hydrocarbon solvent, and the mixtures thereof. Compound I is used at an amount of about 0.005 to 3 moles.

Representative examples of Compound I are suggested with structural formulas below:

Reaction Scheme II

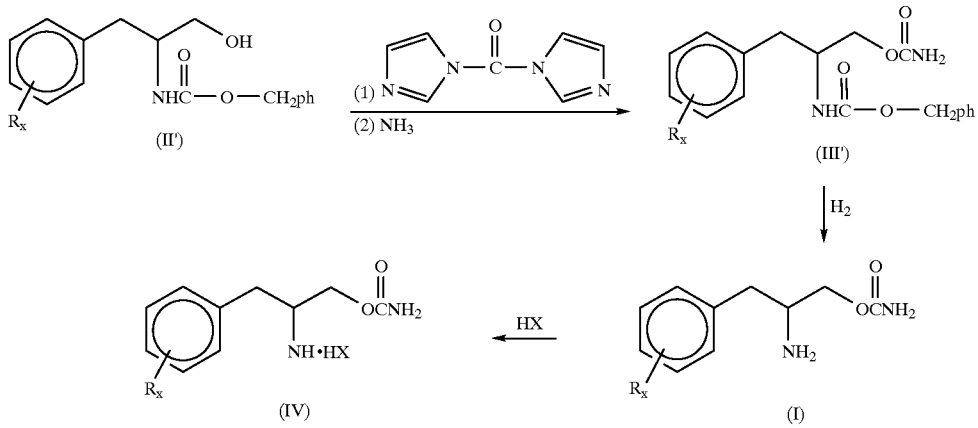

In the reaction scheme II, HX represents an acid capable of forming a pharmacologically useful salt with the basic nitrogen atom.

Details of the reaction conditions described in Reaction Scheme II are as follows. In the first step, the concentration of the starting material (II') is about 0.005 to 3 moles with 1,1'-carbonyldiimidazole ranging from about 1.0 to 2.0 equivalents. This reaction is preferably carried out a temperature of −10 to 70° C. Without purification, the resulting intermediate is treated with 1 to 1,000 equivalents of ammonia at a temperature of −30 to 30° C., to give the compound of the general formula III'. For this carbamoylization, an ethereal solvent such as diethyl ether and tetrahydrofuran, a halogenated hydrocarbon solvent such as dichloromethane and chloroform, or the mixtures thereof may be used.

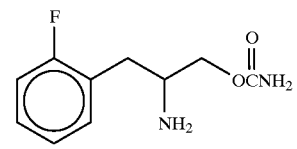

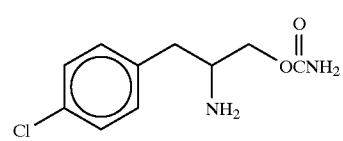

-continued

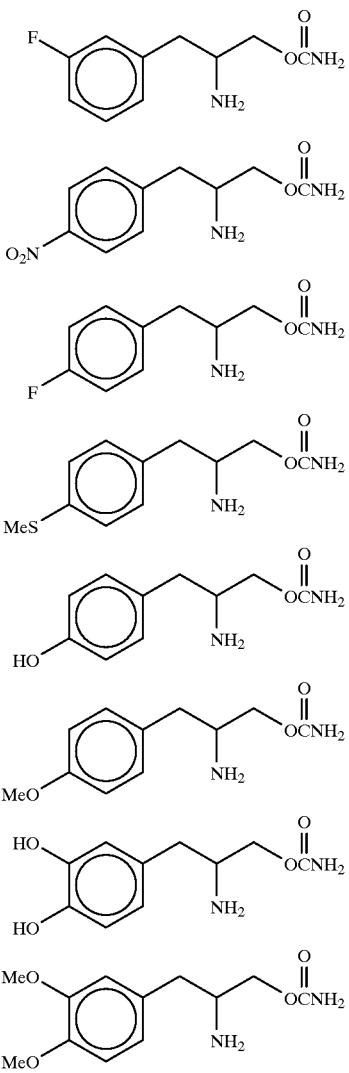

In therapeutic use as agents for various CNS disorders such as depression, anxiety, epilepsy, stroke, demential and Parkinson's disease, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patients, the severity of patient's condition and the activity of the compound. The determination of optimum dosages for a particular situation is within the skill of the art.

In utilizing the compounds of the present invention for the central nervous system, particularly to treat depression, it is preferred to administer the compounds orally. Since the compounds absorb well orally, it usually will not be necessary to resort to parenteral administration. For oral administration, the present compounds are preferably combined with a pharmaceutical carrier. The ratio of the carrier to the present compounds is not critical to express the effects of the medicine on the central nervous system, and they can vary considerably depending on whether the composition is to be filled into capsules or formed into tablets. In tableting, it is usually desirable to employ at least as much pharmaceutical carrier as the pharmaceutically active ingredients.

Various edible pharmaceutical carriers or the mixture thereof can be used. Suitable carriers, for example, are a mixture of lactose, diabasic calcium phosphate and corn starch. Other pharmaceutically acceptable ingredients can be further added, including lubricants such as magnesium stearate.

Besides the above-mentioned compounds, a pharmaceutical composition which comprises as an active ingredient an effective amount of the present compounds is within the scope of the present invention. Furthermore, the present invention includes methods for treating central nervous system disorders which comprises administering an effective amount of the present compounds as an active ingredient.

A better understanding of the present invention may be obtained in light of following examples which are set forth to illustrate, but are not to be construed to limit, the present invention.

EXAMPLE I

Preparation of O-Carbamoyl-N-(t-butyloxycarbonyl)-o-fluorophenylalaninol

In a 250 mL flask equipped with magnetic stirrer, N-(t-butyloxycarbonyl)-o-fluorophenylalaninol (0.096 mole, 2.15 g) was dissolved in 200 ml of THF and was added with 1,1'-carbonyl diimidazole (0.010 mol, 1.62 g) at 0° C. The reaction mixture was stirred at room temperature for 2 hours, followed by the injection of ammonia at 0° C. for 30 min. Following elevating to room temperature, water was added to terminate the reaction. The organic layer was extracted 3 times with dichloromethane, dried over magnesium sulfate and distilled in vacuo, to give a solid. This was recrystallized in a solution mixture of n-hexane and diethyl ether, to produce 1.93 g of O-carbamoyl-N-(t-butyloxycarbonyl)-o-fluorophenylalaninol: Yield 75%.

$^1$H-NMR(CDCl$_3$, 200 MHz), ppm($\delta$): 1.45(s,9H), 2.88(d, 2H), 4.09(s,2H), 4.60–4.83(br,2H), 6.99–7.32(m,4H)

EXAMPLE II

Preparation of O-Carbamoyl-N-(t-butyloxycarbonyl)-p-fluorophenylalaninol

The procedure given in Example I was followed using N-(t-butyloxycarbonyl)-p-fluorophenylalaninol as a starting material, instead of N-(t-butyloxycarbonyl)-o-fluorophenylalaninol, to give 2.91 g of the title compound. A yield of 88% was obtained.

$^1$H-NMR(CDCl$_3$, 200 MHz), ppm($\delta$): 1.45(s,9H), 2.68–2.95(m,2H), 4.02(s,2H), 4.60–4.90(br,2H), 6.85–7.29 (m,4H)

EXAMPLE III

Preparation of O-Carbamoyl-N-(t-butyloxycarbonyl)-p-nitrophenylalaninol

The procedure given in Example I was followed using N-(t-butyloxycarbonyl)-p-nitrophenylalaninol as a starting material, instead of N-(t-butyloxycarbonyl)-o-fluorophenylalaninol, to give 2.66 g of the title compound. A yield of 76% was obtained.

$^1$H-NMR(CDCl$_3$, 200 MHz), ppm($\delta$): 1.25(s,9H), 2.60–2.82(m,1H), 2.85–3.05(m,1H), 3.80–4.10(m,3H), 6.52 (s,1H), 6.90(d.1H), 7.45(d,2H), 8.20(d,2H)

EXAMPLE IV

Preparation of o-Carbamoyl-N-(t-butyloxycarbonyl)-p-(t-butyloxycarbonyloxy) phenylalaninol The procedure given in Example I was followed using N-(t-butyloxycarbonyl)-p-(t-butyloxycarbonyloxy) phenyl alaninol as a starting material, instead of N-(t-butyloxycarbonyl)-o-fluoro phenylalaninol, to give 2.55 g of the title compound. A yield of 68% was obtained.

$^1$H-NMR(CDCl$_3$, 200 MHz), ppm($\delta$): 1.38(s,9H), 1.55(s, 9H), 2.70–2.92(m,2H), 3.68–3.81(m,1H), 3.98–4.12(m,3H), 4.68–4.91(br,2H), 7.01–7.31(m,4H)

EXAMPLE V

Preparation of O-Carbamoyl-N-benzyloxycarbonyl-m-fluorophenylalaninol

In a 100 mL flask equipped with magnetic stirrer, N-benzyloxycarbonyl-m-fluorophenylalaninol (0.007 mole, 2.12 g) was dissolved in 50 ml of THF and was added with 1,1'-carbonyl diimidazole (0.007 mol, 1.14 g) at 0° C. The reaction mixture was stirred at room temperature for 2 hours, followed by the injection of ammonia at 0° C. for 30 min. Following elevating to room temperature, water was added to terminate the reaction. The organic layer was extracted 3 times with dichloromethane, dried over magnesium sulfate and distilled in vacuo, to give a solid. This was recrystallized in a solution mixture of n-hexane and diethyl ether, to produce 2.18 g of O-carbamoyl-N-benzyloxycarbonyl-m-fluorophenylalaninol: Yield 91%.

$^1$H-NMR(CDCl$_3$, 200 MHz), ppm($\delta$): 2.49–2.98(m,2H), 3.69–4.15(m,4H), 4.80–5.12(m,2H), 6.35–6.75 (br,2H), 6.80–7.60(m, 9H)

EXAMPLE VI

Preparation of O-Carbamoyl-o-fluorophenylalaninol Hydrochloric acid Salt

In a 100 mL flask equipped with magnetic stirrer, O-carbamoyl-N-(t-butyloxycarbonyl)-o-fluorophenylalaninol obtained in Example I was dissolved in 40 ml of THF and was added with 20 ml of 6N aqueous hydrochloric acid solution. The reaction mixture was stirred at room temperature for 8 hours, followed by the neutralization with saturated aqueous potassium carbonate solution. Thereafter, the organic layer was extracted 3 times with dichloromethane, dried over magnesium sulfate and distilled in vacuo, to give a yellowish liquid. This, was dissolved in 30 ml of THF and added with anhydrous hydrochloric acid at 0° C., to obtain desirable white precipitates. To this was added 30 ml of anhydrous ether, with the aim of maximizing the precipitation. As a result, 1.22 g of the title compound was obtained: Yield 73%.

Melting point: 160–161° C.

$^1$H-NMR(DMSO-d6, 200 MHz), ppm($\delta$): 2.82–3.18(m, 2H), 3.40–3.70(br,1H), 3.72–4.18(m,2H), 6.62(s,2H), 7.08–7.58(m,4H), 8.45(br,3H)

EXAMPLE VII

Preparation of O-Carbamoyl-p-fluorophenylalaninol Hydrochloric acid Salt

The procedure given in Example VI was followed using O-carbamoyl-N-(t-butyloxycarbonyl)-p-fluorophenylalaninol as a starting material, to give the title compound.

Melting point: 111–113° C.

$^1$H-NMR(DMSO-d6, 200 MHz), ppm($\delta$): 2.85–3.20(m, 2H), 3.20–3.60(br,1H), 3.80–4.20(m,2H), 6.65(s,2H), 6.98–7.45(m,4H), 8.45(br,3H)

EXAMPLE VIII

Preparation of O-Carbamoyl-p-nitrophenylalaninol Hydrochloric acid Salt

The procedure given in Example VI was followed using O-carbamoyl-N-(t-butyloxycarbonyl)-p-nitrophenylalaninol obtained in Example III as a starting material, to yield the title compound.

$^1$H-NMR(CDCl$_3$, 200 MHz), ppm($\delta$): 3.04(d-d,1H), 3.22 (d-d,2H), 3.67(br,1H), 3.94(d-d,1H), 4.06(d-d,1H), 6.63(s, 2H), 7.62(d,2H), 8.24(d,2H), 8.53(br,3H)

EXAMPLE IX

Preparation of O-Carbamoyl-p-hydroxy phenylalaninol Hydrochloric acid Salt

The procedure given in Example VI was followed using O-carbamoyl-N-(t-butyloxycarbonyl)-p-(t-butyloxycarbonyl oxy) phenylalaninol obtained in Example IV as a starting material, to yield the title compound.

Melting point: 213°–214° C.

$^1$H-NMR(DMSO-d6, 200 MHz), ppm($\delta$): 2.58–3.11(m, 2H) 3.50–3.72(br,1H), 3.78–4.15(m,2H), 6.65(s,2H), 7.10 (d,2H), 8.35(br,3H), 9.48(s,1H)

EXAMPLE X

Preparation of O-carbamoyl-m-fluoro phenylalaninol Hydrochloric acid Salt

In a 500 mL Parr reactor, o-carbamoyl-N-benzyloxy carbonyl-m-fluoro phenylalaninol (0.006 mole, 2.18 g) obtained in Example V was dissolved in 50 mL of anhydrous methanol and added with palladium (carbon powder 10%, 0.10 g). Then, the reactor was closed and purged with hydrogen. The reaction was completed in 7 hours under hydrogen pressure of 50 psi at room temperature, which was confirmed on thin layer chromatography. The catalyst was filtered off. Thereafter, the organic layer thus obtained was concentrated through distillation into 1.08 g (99%) of pale yellow liquid. The liquid was poured in 30 mL of anhydrous THF and cooled to 0° C. Anhydrous hydrochloric acid was then added, to give a desirable white precipitate. Addition of 30 mL of anhydrous ether maximized the precipitation. Filtration provided 1.24 g of the title compound.

Melting point: 144–145° C.

$^1$H-NMR(DMSO-d6, 200 MHz), ppm($\delta$): 2.85–3.15(m, 2H), 3.50–3.72(br,1H), 3.82–4.15(m,2H), 6.65(s,2H), 7.08–7.28(m,3H), 7.30–7.51(m,1H), 8.38(br,3H)

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. An O-carbamoyl-phenylalaninol compound having a substituent at the benzene ring, represented by the following structural formula I:

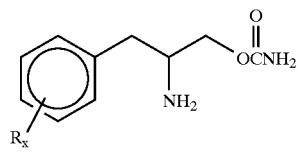

[I]

wherein R is selected from the group consisting of lower alkyl containing 1 to 8 carbon atoms, halogen selected from the group consisting of F, Cl and I, alkoxy containing 1 to 3 carbon atoms, thioalkoxy containing 1 to 3 carbon atoms, nitro, hydroxy, and trifluorocarbon, and x is an integer from 1 to 3, with the proviso that R is the same or different when x is 2 or 3, or a pharmaceutically acceptable salt thereof.

2. The compound in accordance with claim 1, wherein the O-carbamoyl-phenylalaninol compound having substituent at benzene ring comprises the compounds having the following structural formulas:

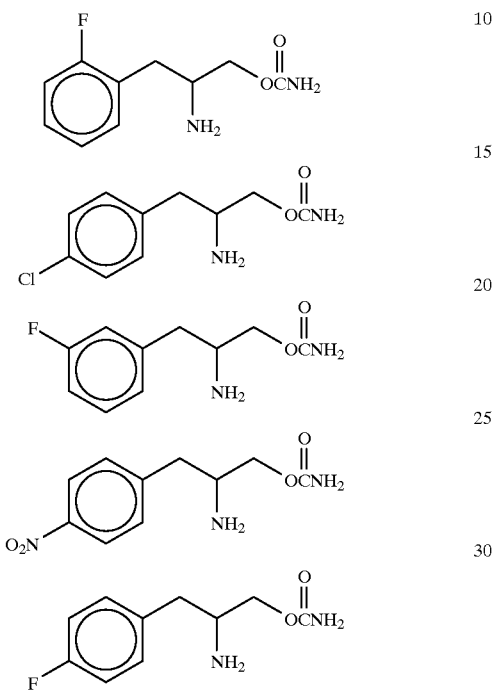

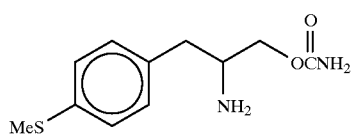

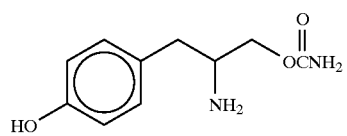

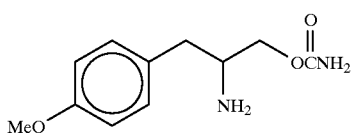

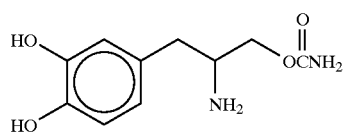

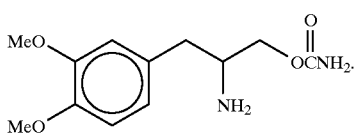

* * * * *